United States Patent [19]

Van den Berg

[11] Plant 4,742

[45] Jun. 16, 1981

[54] BEGONIA PLANT

[75] Inventor: Cornelis P. Van den Berg, Ashtabula, Ohio

[73] Assignee: Mikkelsens Inc., Ashtabula, Ohio

[21] Appl. No.: 132,328

[22] Filed: Mar. 20, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A begonia plant known by the cultivar name Harmony having large, double, light orange flowers and dark green foliage; a relatively great number of pistillated flowers; early flowering and floriferous habit; excellent keeping quality; adaptability in a controlled environment to year round flowering and varying pot size; sturdy, upright and compact growth habits, and excellent vigor.

1 Drawing Figure

The present invention relates to a new and distinctive cultivar of begonia plant, botanically known as Begonia × hiemalis Fotsch, and hereinafter referred to by the cultivar name Harmony.

The new cultivar was discovered by me as a seedling from a controlled crossing of a Begonia × tuber hydrida cultivar as the seed parent with a *Begonia socotrana* cultivar as the pollen parent.

Asexual reproduction by stem and/or leaf cuttings in Ashtabula, Ohio has confirmed that the unique characteristics of the new cultivar are reproduced true to form through successive propagations.

The following characteristics distinguish Harmony from both its parents and other begonias commercially known and used in the floriculture industry:

1. Harmony has large, double, light orange flowers, pleasantly contrasting with the dark green foliage.
2. Harmony exhibits more pistillated flowers than normal in this type of begonia, with generally one third of the flowers formed being pistillated.
3. Harmony is early flowering and floriferous, with a good placement of the flowers over the leaf canopy.
4. The keeping quality of the plant and the individual flowers is excellent both in the greenhouse and in the home.
5. The new cultivar can be flowered year round by proper manipulation of the controlled environment.
6. The cultivar can be grown in a 10 cm. pot, or up to 15 cm. pot, again by a properly controlled environment.
7. Harmony has a sturdy, upright growth with a compact growth habit.
8. Overall plant vigor is excellent, with strong stems, good self support, strong petioles and strong peduncles.

The accompanying colored photograph illustrates the new cultivar, with the colors being as true as it is reasonably possible to obtain in a colored reproduction of this type.

The following is a detailed description of my new begonia cultivar based on plants produced under commercial practices in the greenhouses of Mikkelsens Inc., Ashtabula, Ohio. Color references are made to the Royal Horticultural Society Colour Chart except where general color terms of ordinary dictionary significance are used.

Parentage:

A controlled cross of Mikkelsen seedling 76-61-18, a Begonia × tuber hybrida, as the seed parent and Mikkelsen seedling 73-60S, a *Begonia socotrana,* as the pollen parent.

Propagation:

(A) *Type cutting.*—Leaf cuttings.

(B) *Time to root.*—3 to 4 weeks at temperature of the growing medium of 21° C.

(C) *Rooting habit.*—Fine, fibrous.

(D) *Time for shoot development.*—10 weeks in summer to 14 weeks in winter, to obtain shoots of approximately 4–5 cm. in length.

Plant description:

(A) *Form.*—Compact, close internoded, upright, with good vigor for self support. Growing and scheduling practices can produce a small plant in a 10 cm. pot, up to a larger plant in a 15 cm. pot.

(B) *Habit of growth.*—Rate of growth moderate for this type of begonia. Generally, vegetative shoots are formed at the basal nodes and flowers at the higher nodes.

(C) *Foliage.*—Leaves simple, alternate, borne on strong petioles, 5 mm. in diameter when fully grown. (1) Size: Varying as to the position on the plant and the environment; up to 10 × 12 cm. when full grown. (2) Shape: Ovate to nearly round, basal lobes overlapped. (3) Texture: Glabrous, leathery. (4) Margin: Crenate to dentate. (5) Color: young foliage top side, green 137B, under side yellow-green 147C, slightly infused with red mature foliage top side, green 137C, under side yellow-green 147C, slightly infused with red. (6) Veination: 7–8 veins.

Flowering description:

(A) *Flowering habit.*—Flowers in cymes, generally consisting of 2 lower double flowers and 1 pistillated terminal flower; lower flower develops first, pistillated flower last; sometimes pistillated flower will not develop or drops in an early stage of development.

(B) *Natural flowering season.*—Throughout the year, plant will flower in an earlier stage of development under short day conditions.

(C) *Flower bud description.*—Nearly round, up to 30 mm. in diameter before opening, pistillated flower conical, generally with one sepal sticking out of one side, up to 18 mm. long before opening.

(D) *Flowers borne.*—On strong peduncles, up to 5 mm. in diameter, at the base yellow-green 151A, toward the top infused with red, near the flower slightly darker than orange-red 34B.

(E) *Quantity.*—Primary shoots at higher nodes; 1 peduncle per leaf, generally with 3 flowers. Secondary shoots generally have 1 peduncle per leaf, starting from the base, also with 3 flowers. Overall floriferous.

(F) *Tepals.*—(1) Shape: Nearly round. (2) Color: Top side in winter when opening, margin of outer petals red 44D, changing to red 40D toward center; second set of petals, margin red 41C, changing to red 40D toward center; inside petals gradually changing to red 40C toward center petals, fading generally to red 41C; under side red 43C. (3) Number of tepals: Average of 20 on male flowers, 6 on female flowers. (4) Size of tepals: Outer petals 30 mm. in diameter, center petals being as small as 12 mm. in diameter. (5) Flower size: Average of 50 mm. in diameter.

(G) *Reproductive organs.*—(1) Stamens: None observed to date. (2) Pistels: (a) Stigma shape: twisted, color yellow 13A. (b) Style color: Translucent green. Generally styles and stigmas are degenerated in an early stage and are green-brown to brown. (c) Ovary: Inferior, 3 celled, 3 angled, the angle extending into 3 unequal wings; color of ovary light green, slightly infused with red, wings more heavily infused with red.

Disease resistance:

Under normal growing conditions for begonias Harmony exhibits excellent resistance against powdery mildew.

I claim:

1. A new and distinct cultivar of begonia plant known by the cultivar name Harmony, as described and illustrated, and particularly characterized as to uniqueness by its large, double, light orange flowers and dark green foliage; relatively great number of pistillated flowers; early flowering and floriferous habit; excellent keeping quality; adaptability in a controlled environment to year round flowering and varying pot size; sturdy, upright and compact growth habits, and by its excellent vigor.

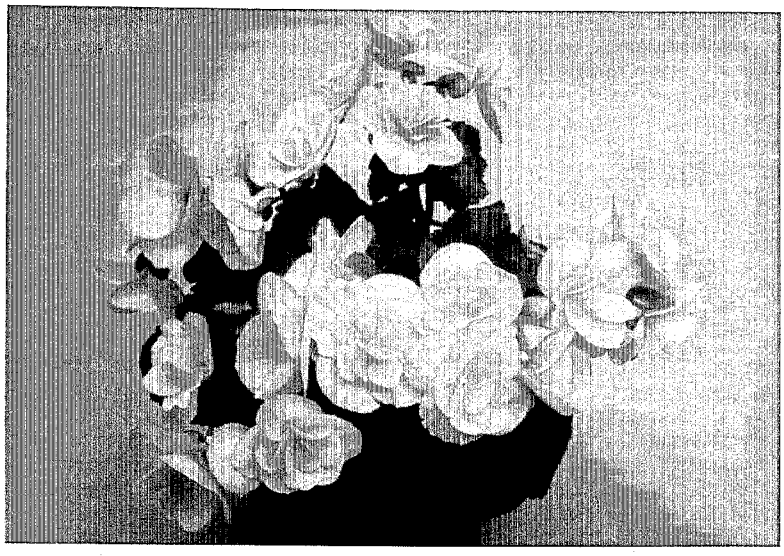

* * * * *